United States Patent [19]

Shimizu et al.

[11] Patent Number: 4,925,981
[45] Date of Patent: May 15, 1990

[54] METHOD OF ISOLATING METHACRYLIC ACID

[75] Inventors: Noboru Shimizu, Takatsuki; Hiroshi Yoshida, Toyonaka; Hiromiki Daigo, Minoo; Shoichi Matsumoto, Ikeda, all of Japan

[73] Assignee: Nippon Shokubai Kagaku Kogyo Co., Ltd., Osaka, Japan

[21] Appl. No.: 3,864

[22] Filed: Jan. 16, 1987

Related U.S. Application Data

[63] Continuation-in-part of Ser. No. 800,093, Nov. 20, 1985, which is a continuation of Ser. No. 458,536, Jan. 17, 1983, abandoned.

[30] Foreign Application Priority Data

Jan. 22, 1982 [JP] Japan .................................. 57-7492

[51] Int. Cl.$^5$ ............................................. C07C 51/48
[52] U.S. Cl. .................................... 562/600; 562/532; 562/538; 562/545
[58] Field of Search ......................................... 562/600

[56] References Cited

U.S. PATENT DOCUMENTS

| | | | |
|---|---|---|---|
| 3,388,897 | 6/1968 | Calaceto | 261/111 |
| 3,405,172 | 10/1968 | Brown et al. | 260/530 |
| 3,433,840 | 3/1969 | Shima et al. | 260/604 |
| 3,664,968 | 5/1972 | Eden | 252/437 |

FOREIGN PATENT DOCUMENTS

| | | | |
|---|---|---|---|
| 56-113732 | 9/1981 | Japan | 562/545 |
| 57-91944 | 6/1982 | Japan | 562/600 |
| 2004886 | 4/1979 | United Kingdom | 562/600 |

OTHER PUBLICATIONS

Nippon Kayaku Co., Ltd., Chemical Abstracts, vol. 96, No. 35874x (1982).

*Primary Examiner*—Bruce D. Gray
*Attorney, Agent, or Firm*—Sherman & Shalloway

[57] ABSTRACT

A method of isolating and recovering methacrylic acid from a methacrylic acid-containing reaction product gas resulting from the vapor-phase catalytic oxidation of isobutylene, tertiary butanol or isobutyraldehyde, which comprises introducing the reaction product gas comprising methacrylic acid and various by-products including high boiling substances at a high temperature of 250° to 300° C. into a cooling zone, rapidly cooling the gas therein to a temperature of not more than 100° C. to condense methacrylic acid and thus isolate methacrylic acid, while also converting the high boiling substances to fumes, thereafter introducing the cooled gas containing said fumes into a venturi scrubber, contacting it therein with an aqueous medium to remove said fumes, finally introducing the treated gas into a methacrylic acid-absorbing zone and absorbing methacrylic acid by absorption into an aqueous medium.

5 Claims, 1 Drawing Sheet

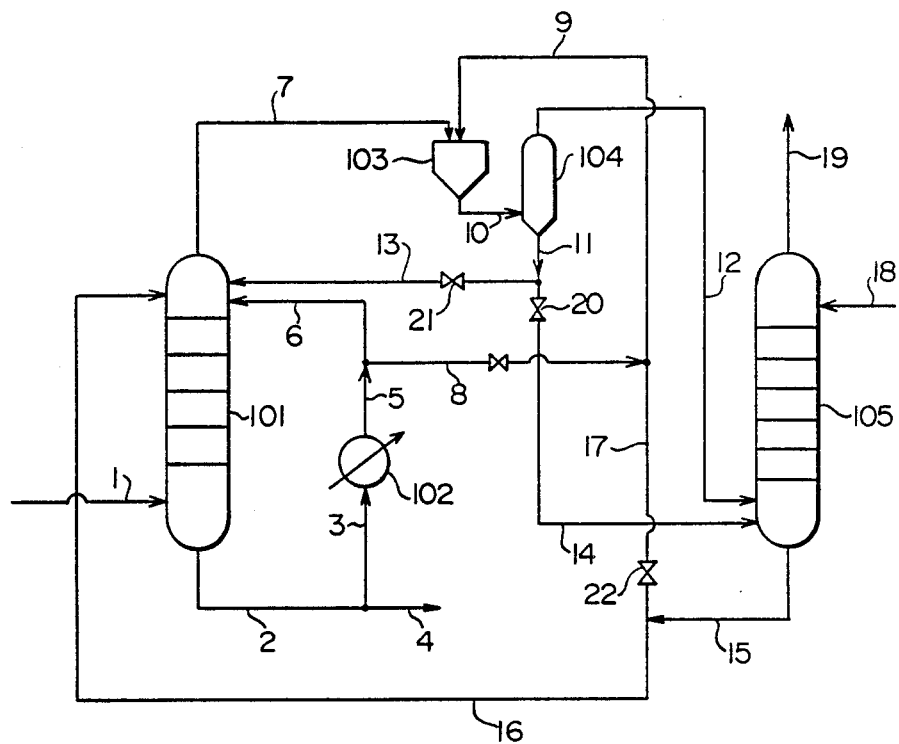

METHOD OF ISOLATING METHACRYLIC ACID

This application is a continuation-in-part application of U.S. Ser. No. 800,093, which is a continuation application of U.S. Ser. No. 458,536abandoned.

This invention relates to a method of isolating methacrylic acid. More specifically, it pertains to a method of isolating methacrylic acid stably with industrial advantage from a methacrylic acid-containing reaction product obtained by the vapor-phase catalytic oxidation reaction of isobutylene, tertiary butol or isobutyraldehyde.

It has recently been known from many literature references that methacrylic acid can be produced by catalytically oxidizing a compound having 4 carbon atoms such as isobutylene, tertiary butanol or isobutyraldehyde in the vapor phase. It is true, however, that methacrylic acid has not yet been produced industrially by vapor-phase catalytic oxidation. This is presumably because an oxidation catalyst having sufficient performance has not been developed and it is extremely difficult to separate methacrylic acid effectively from the by-products in the reaction product (namely, various troubles in the methacrylic acid purifying step have not been removed). The reaction product gas contains, in addition to methacrylic acid, various by-products for example methacrolein, acrolein, acrylic acid, acetic acid, acetaldehyde, carbon monoxide, carbon dioxide, maleic acid, aromatic carboxylic acids (such as benzoic acid and terephthalic acid), and tarry substances. The present inventors found as indicated below that among these by-products, relatively high-boiling substances cause various troubles in the step of isolating methacrylic acid from the reaction product gas.

According to a conventional method, the gas leaving the oxidation reactor is pre-cooled to 150° to 200° C. for recovery of heat before it is introduced into a scrubber to isolate methacrylic acid. However, in the case of the catalytic vapor-phase oxidation of the aforesaid compounds having 4 carbon atoms, cooling of the reaction product gas in a pre-cooler results in the precipitation of the high-boiling substances existing in fairly large amounts in the product gas on the heat exchanging surface of the pre-cooler, and the pre-cooler is blocked up within a relatively short period of time. It is desirable therefore to introduce the reaction product gas at high temperatures directly into the methacrylic acid scrubber without pre-cooling. Since the reaction temperature in the aforesaid oxidation reaction is 280° to 340° C., the reaction product gas leaving the oxidation reactor is generally at these temperatures.

When this reaction product gas at high temperatures is introduced into a cooling zone of the methacrylic acid scrubber and directly contacted with a cooling medium, preferably an aqueous solution of methacrylic acid, the gas is rapidly cooled, and a greater portion of methacrylic acid is scrubbed as an aqueous solution of methacrylic acid, but the aforesaid high-boiling substances are converted into fumes as a result of rapid cooling and most of them are likely to be discharged together with the gas from the cooling zone. Of course, some of the high-boiling substances dissolve in the aqueous solution of methacrylic acid.

Since the gas containing the fumes contains a considerable amount of methacrylic acid, it is then introduced into a methacrylic acid-absorbing zone, and methacrylic acid in the gas is absorbed by water or an aqueous solution of methacrylic acid flowing down from the top of the absorbing zone. The fumes in the gas, however, are partly precipitated as a solid in the absorbing zone to block up packings such as Raschig rings or holes of a sieve tray with a downcomer. Since the gas leaving the methacrylic acid-absorbing zone contains methacrolein, it is necessary to recover methacrolein as an aqueous solution by introducing this gas into a methacrolein-absorber. In the methacrolein-absorber, there is little problem attributed to the fumes. However, in a so-called three-stage reaction in which the gas containing methacrolein is fed without recovering methacrolein from it to the next oxidation reactor so as to oxidize the remaining methacrolein to methacrylic acid, the fumes inevitably go to the third reactor and precipitate as a solid at the inlet portion of the reactor, resulting in an increase in the pressure drop of the reactor bed. Even when methacrolein is recovered, the gas discharged from the methacrolein-absorber, contains a considerable amount of the fumes entrained therein. When this discharge gas is utilized as an inert gas for the first and/or second reactors, troubles, such as the precipitation of the fumes in a recycling blower and in the inlet portions of the first and/or second reactors, are likely to occur. Furthermore, when the discharge gas from the methacrolein-absorber is burned to make it non-toxic, a trouble of the precipitation of the fumes as a solid occurs in a heat exchanger for gas preheating.

In short, the fumes generated because of rapid cooling in the cooling zone of the methacrylic acid scrubber cause many troubles, for example the blocking of the methacrylic acid-absorbing zone, the third reactor, the recycle blower, the inlet portions of the first and/or second reactors, and the heat exchanger for preheating of the discharge gas.

The fumes are generated because the gas at high temperatures is rapidly cooled upon direct contact with an aqueous solution of methacrylic acid which is kept at a relatively low temperature. The particle diameter of the fumes is considerably small.

It is an object of this invention to provide a method of isolating methacrylic acid in which the fumes can be effectively trapped to remove the various troubles attributed to the fumes.

Investigations of the present inventors have led to the discovery that when the reaction product gas is cooled to a temperature below 100° C. in a cooling zone to generate fumes, and the gas containing the resulting fumes is washed by a venturi scrubber, most of the fumes can be collected.

Thus, according to this invention, there is provided a method of isolating and recovering methacrylic acid from a methacrylic acid-containing reaction product gas resulting from the vapor-phase catalytic oxidation of isobutylene, tertiary butanol or isobutyraldehyde, said method comprising introducing the reaction product gas comprising methacrylic acid and various by-products including high boiling substances at a high temperature of 250° to 300° C. into a cooling zone, rapidly cooling the gas therein to a temperature of not more than 100° C. to condense methacrylic acid and thus isolate methacrylic acid, while also converting the high boiling substances to fumes, thereafter introducing the cooled gas into a venturi scrubber, contacting it therein with an aqueous medium to remove said fumes, finally introducing the treated gas into a methacrylic acid-absorbing zone and absorbing methacrylic acid with an aqueous medium.

The method of this invention will be described below more specifically.

In a first reactor, isobutylene, tertiary butanol or isobutyraldehyde is oxidized mainly to methacrolein. The reaction product gas leaving a second reactor in which methacrolein is oxidized to methacrylic acid is usually at a temperature of 280° to 340° C. As required, this reaction product gas at high temperatures may be cooled to 250° C., but usually without pre-cooling, it is introduced into a cooling zone of a methacrylic acid-scrubber.

In the cooling zone, the gas is rapidly cooled to 100° C. or below, preferably 70° C. or below, by directly contacting it with a downwardly flowing aqueous solution of methacrylic acid as a cooling medium. Preferably, the aqueous solution of methacrylic acid has a temperature of 30° to 70° C. and a concentration of 10 to 50% by weight.

The cooling zone in which the gas is contacted directly with the aqueous methacrylic acid solution is constructed preferably of a sieve tray without a downcomer. The hole size of the tray is preferably at least 10 mm, especially at least 20 mm. An attempt to use Raschig rings in place of the sieve tray without a downcomer tends to cause blocking of the column by a solid material during long-term operation.

The gas leaving the cooling zone is conducted to a venturi scrubber, and subjected to jet atomizing together with water or an aqueous solution of methacrylic acid fed therein, whereby a greater portion of the fumes is collected. White solid suspended particles are floating in the liquid which leaves the venturi scrubber at this time. The bottom liquid in the cooling zone or a bottom liquid in a methacrylic acid absorbing zone to be described is preferred as the aqueous solution of methacrylic acid. Preferably, the aqueous methacrylic acid solution has a concentration of 5 to 50% by weight and a temperature of 30° to 70° C. The liquid which leaves the venturi scrubber is recycled to the cooling zone when the bottom liquid in the cooling zone is used, and to the absorbing zone when the bottom liquid of the absorbing zone is used.

The present inventors have found that particles of the fumes generated by rapid cooling in the cooling zone are as fine as about 0.1 to 5 microns, and cannot be collected by an ordinary washing device (e.g., a packed column), a jet scrubber, a cyclone, etc., and that they can be effectively trapped only by a venturi scrubber in which the gas and water or an aqueous solution of methacrylic acid are subjected to jet atomizing.

The liquid leaving the venturi scrubber may be returned to the respective portions after the solid has been separated as desired. The solid in this liquid is extremely fine and cannot be separated by usual filtration measures. Accordingly, only a centrifugal separator having a high G value or a filtration device with an opening size of less than several tens of microns can be used.

The venturi scrubber used in this invention may be a usual type such as a device comprised of a combination of a venturi and a cyclone, and its specification is not particularly limited. Operating conditions for the venturi scrubber are such that the suitable flow rate of the gas at its throat portion is in the range of 30 to 100 meters/second, and the suitable liquid/gas ratio (liter of the liquid/m$^3$ of the gas) is in the range of 0.5 to 2.

The gas leaving the venturi scrubber is conducted to a methacrylic acid absorbing zone where methacrylic acid is absorbed and recovered. Preferably, this absorbing zone is also constructed of a sieve tray without a downcomer. When a column packed with Raschig rings or a sieve tray with a downcomer is used, the Raschig rings or the sieve holes tend to be blocked up during long-term operation.

The method of this invention is described in more detail with reference to its preferred embodiments taken in conjunction with the accompanying drawing which is a flow sheet showing one example of a process for isolating methacrylic acid in accordance with the method of this invention.

The reaction product gas obtained by the vapor-phase catalytic oxidation of isobutylene, tertiary butanol or isobutyraldehyde is usually at a temperature of 280° to 340° C. This product gas at high temperatures (which may, as required, be cooled up to 250° C.) is introduced into a methacrylic acid cooling column 101 through a line 1 without pre-cooling.

In the methacrylic acid cooling column 101, the gas is rapidly cooled to 100° C. or below, preferably to 70° C. or below, by directly contacting it with a downwardly flowing aqueous solution of methacrylic acid introduced mainly from a line 6. The aqueous solution of methacrylic acid introduced into the cooling column 101 is circulated through a line 2, a line 3, a cooler 102, a line 5 and a line 6, and an increment is withdrawn from a line 4 and then submitted to after-treatment steps such as separation and purification (not shown). The aqueous methacrylic acid solution circulated is cooled at 30° to 70° C., and the concentration of methacrylic acid is adjusted to a range of 10 to 50% by weight.

The gas leaving the cooling column 101 is introduced through a line 7 into a venturi 103 where it is subjected to jet atomizing together with water or an aqueous solution of methacrylic acid introduced through a line 9. As a result, most of the fumes are trapped by water or the aqueous methacrylic acid solution. The gas-liquid mixture atomized in the venturi 103 is then introduced into a cyclone 104 through a line 10, and separated therein into a liquid and a gas.

When an aqueous methacrylic acid solution is fed to the venturi 103 for trapping of the fumes, the bottom liquid of the cooling column 101 is introduced through lines 2, 3, 5, 8 and 9 or the bottom liquid of the absorber 105 through lines 15 and 9. This aqueous methacrylic acid solution is adjusted to a concentration of 5 to 50% by weight and a temperature of 30° to 70° C.

When the bottom liquid of the cooling column 101 is used for trapping of the fumes, the liquid which leaves the cyclone 104 is recycled to the cooling column 101 through lines 11 and 13 (at this time, a valve 20 of line 14 is shut). When the bottom liquid of the absorber 105 is used for trapping of the fume, the liquid leaving the cyclone 104 is recycled to the absorber 105 through lines 11 and 14 (at this time, a valve 21 of the line 13 is shut).

In the meantime, the gas leaving the cyclone 104 is introduced into the absorber 105 and is contacted countercurrently with water or an aqueous methacrylic acid solution introduced through a line 18, and a greater portion of methacrylic acid in the gas is absorbed. A gas is discharged from the top of the absorber 105 through a line 19, and this gas is sent to a methacrolein-absorber (not shown).

Preferably, a polymerization inhibitor, such as hydroquinone, or hydroquinone monomethyl ether, is included in water or a methacrylic acid solution introduced through the line 18. The aqueous methacrylic acid solution at the bottom of the absorber 105 is discharged through line 15, and when a valve 22 in a line 17 is shut, all of the aqueous methacrylic acid solution is introduced into the cooling column 101 through line 16. When the valve 22 of the line 17 is open, only an increment is introduced into the cooling column 101 through the line 16.

By employing the method of this invention described hereinabove, (1) the blocking of the inlet portion of the third reactor, (2) the blocking of the methacrylic acid absorbing zone, (3) the blocking of the inlet portion of the blower and the inlet portion of the reactor in the case of recycling the waste gas of the methacrolein-absorber to the first reactor as an inert gas, and (4) the blocking of a pre-heater for combustion of the waste gas can be removed, and all of the troubles attributed to the generation of the fumes in the oxidation step have been eliminated. According to the method of this invention, therefore, a three-stage reaction becomes possible, and recycling or burning of the waste gas can be performed for a long period of time without any trouble. As a result, a great industrial advantage is brought about by the method of this invention.

The following non-limitative Examples illustrate the present invention.

EXAMPLE 1 t-Butanol was oxidized in two stages with air in the presence of steam using the molybdenum-type complex oxide described in Example 18 of U.S. Pat. No. 3,825,600 as a first-stage catalyst and the heteropolyacid-type compound of the molybdenumphosphorus series described in Example 22 of EP No. 0043100 as a second-stage catalyst. The outlet gas (reaction product gas) of the second reactor was obtained in an amount of 25 $Nm^3$ per hour. This gas consisted of 0.8% by volume of methacrolein, 2.8% by volume of methacrylic acid, 25.0% by volume of steam and the remainder being nitrogen, oxygen, carbon monoxide and carbon dioxide and small amounts of by-products, and had a temperature of 300° C. This gas was subjected to an operation of isolating methacrylic acid.

Without cooling, the reaction product gas at 300° C. was introduced into a cooling column and directly contacted countercurrently with an about 25% by weight aqueous solution of methacrylic acid at 40° C. flowing from the top of the cooling column to cool the gas rapidly from 300° C. to 50° C. to isolate methacrylic acid as an aqueous solution. The cooling column is a stainless steel tower having an inside diameter of 150 mm and including sieve trays without a downcomer, in which fifteen trays having a hole size of 25 mm and 19.4% hole area were arranged with a tray spacing of 200 mm.

The gas which left the cooling column was then introduced into a venturi scrubber consisting of a venturi and a cyclone. The ca. 25% by weight aqueous solution of methacrylic acid, which was the bottom liquid of the cooling column, was fed as a washing liquid at a rate of 38 kg per hour. The liquid discharged from the venturi scrubber was whitely turbid. This liquid was returned to the top of the cooling column. The gas leaving the venturi scrubber was at 40° C. It was sent to the lower portion of a methacrylic acid-absorber, and methacrylic acid was absorbed by water at 30° C. flowing down from the top of the absorber at a rate of 5 kg/hour. The methacrylic acid-absorber was a stainless steel tower having an inside diameter of 150 mm and including a sieve tray without a downcomer, in which twenty trays having a hole size of 12 mm and 10.2% hole area were arranged with a tray spacing of 150 mm. The bottom liquid of the methacrylic acid-absorber was recycled to the top of the cooling column. The total amount of methacrylic acid isolated through the cooling column, the venturi scrubber and the methacrylic acid-absorber was 09%.

The gas leaving the top of the methacrylic acid-absorber was divided into two portions. One portion was sent to a methacrolein-absorber where a greater portion of methacrolein was absorbed with cold water at an operating temperature in the range of 10° to 15° C. The waste gas at a temperature of about 10° C. from the methacrolein-absorber was first pre-heated to about 200° to 250° C. in a multi-tube heat exchanger where the waste gas was heated with a burnt gas. Then, the pre-heated gas was burned in a catalyst bed. This pre-heater was comprised of a multiplicity of stainless steel tubes with a diameter of ½ inch.

The other portion of the gas from the top of the methacrylic acid-absorber was introduced directly into a third reactor where methacrolein contained in the gas was oxidized to methacrylic acid. This reactor had the same catalyst as the second-stage one, and the temperature of the heat medium was 300° C.

The aforesaid operations were each carried out for 2 months. During this time, no increase in pressure drop was noted at the respective parts, and the operation could be continued without a trouble. After the operation, the inside of each of the parts was inspected. There was scarcely any blocking, owing to the fumes, of the cooling column, methacrylic acid-absorber, the methacrolein-absorber, the waste gas pre-heater and the catalyst layer of the third reactor.

COMPARATIVE EXAMPLE 1

Methacrylic acid was isolated in the same way as in Example 1 except that no Venturi scrubber was provided after the cooling column.

After operating for 1 week, the pressure drop in the waste gas pre-heater became more than three times as large as that in the initial stage, and the pressure drop of the catalyst layer in the third reactor reached more than two times that in the initial stage. The operation was therefore stopped, and the inside of the apparatus was inspected. In the methacrylic acid-absorber, white solids were found to be deposited to a thickness of 1 to 2 mm around the holes of trays, on the upper side and backside of trays, and on the inner wall of column, but not to such an extent as to cause clogging of the holes. A yellowish brown solid precipitated on the inside of the heat-exchanger tube of the waste gas pre-heater to block it up in part. Furthermore, a blackish brown solid filled the catalyst layer at the inlet portion of the third reactor.

COMPARATIVE EXAMPLE 2

In Example 1, the cooling column was changed to a packed column including 1-inch Raschig rings. The methacrylic acid-absorber was changed to sieve trays having a hole size of 6 mm and 10% hole area with a downcomer, and the position of providing the venturi scrubber was changed to the exit of the methacrylic acid-absorber. Furthermore, the washing liquid fed at a rate of 38 kg/hr to the venturi scrubber was changed to water at 30° C. The discharge liquid from the venturi scrubber was fed into the top of the methacrylic acidabsorber to use it for absorbing methacrylic acid. Otherwise, the same operation as in Example 1 was carried out.

After the operation of 1 week, the pressure drop in the absorber became twice as high as that at the initial stage. The operation was therefore stopped, and the inside of the apparatus was inspected. It was found that no change occurred in the waste gas pre-heater and the third reactor provided after the venturi scrubber. But about half of the holes of several trays at the lower portion of the absorber were blocked up with a yellowish white solid.

COMPARATIVE EXAMPLE 3

Example 1 was followed except that a cyclone scrubber, a spray tower or a sieve tray column without downcomer each having the specification shown below was used instead of the venturi scrubber to wash the gas, and methacrylic acid was isolated.

|  | Cyclone scrubber | Spray tower | Sieve tray column without downcomer |
|---|---|---|---|
| Inside diameter | 150 mm | 150 mm | 150 mm |
| Height | 2 m | 2 m | 2 m |
| Flow rate of the liquid | 500 kg/hr | 500 kg/hr | 50 kg/hr |
| Internal structure | Jetting from a central tube | Three-stage spraying | Ten trays having a hole size of 10 mm and 12% hole area with a tray spacing of 150 mm |

In all of these cases, solids adhered to a thickness of 1 to 2 mm to the sieve trays of the methacrylic acid-absorber after operation for one week. and the heat-exchanger tubes of the waste gas pre-heater were partly blocked up. Furthermore, the pressure drop of the third reactor was doubled.

COMPARATIVE EXAMPLE 4

In the method described in Example 1, the reaction product gas at 300° C. was first passed through a cooler to cool it to 200° C., and then sent to the cooling column. The cooler was of a stainless steel multitube heat exchanger composed of heat-exchanger tubes having an inside diameter of 1 inch, and a heat medium at 180° C. was circulated through its external shell.

In 5 days, the pressure drop of the cooler was 1.5 times that in the initial stage. The operation was therefore stopped and the inside of the cooler was inspected. It was found that the surfaces of the heat-exchanger tubes were blocked up with a large amount of blackish brown solid.

EXAMPLE 2

Using the heteropolyacid type compound containing molybdenum and phosphorus described in Example 42 of EP No. 0043100, isobutyraldehyde was oxidatively dehydrogenated with air in the presence of steam to obtain a reactor outlet gas in an amount of 25 Nm³ per hour. This gas consisted of 0.35% by volume of methacrolein, 3.0% by weight of methacrylic acid, 25% by volume of steam and the remainder being nitrogen, oxygen, carbon monoxide, carbon dioxide and small amounts of by-products, and had a temperature of 300° C. This gas was subjected to the same isolating operation as in Example 1.

The gas which left the top of the methacrylic acid-absorber was divided into two portions. One portion was sent to a methacrolein-absorber and treated in the same way as in Example 1.

The other portion was introduced directly into a second reactor where methacrolein contained in the gas was oxidized to methacrylic acid. This reactor included the same catalyst as used in the first reactor, and the temperature of the heat medium therein was 300° C.

The above operation was continued for 2 months. During this period, no increase in pressure drop was noted in any part of the apparatus, and the operation could be performed without a trouble. After the operation, the inside of the apparatus was inspected, but there was scarcely any blocking, owing to the fumes, of the cooling column, methacrylic acid-absorber, the methacrolein-absorber, the waste gas pre-heater, and the catalyst layer in the second reactor.

EXAMPLE 3 AND COMPARATIVE EXAMPLE 5 AND 6

Example 1 was repeated except that the temperature of the outlet gas (reaction product gas) was changed to 290° C. (Example 3), 310° C. (Comparative Example 5) or 320° C. (Comparative Example 6). Changes in pressure drop with time in the catalyst layer of the third reactor were measured. The results are shown in the following table.

| | | | Comparative Example | |
|---|---|---|---|---|
| Temperature of the outlet gas (°C.) | | Example 3 290 | 5 310 | 6 320 |
| (*) Change of the pressure drop ratio with the passage of time | Start | 1.0 | 1.0 | 1.0 |
| | After 3 days | 1.0 | 1.0 | 1.0 |
| | After 7 days | 1.0 | 1.0 | 1.0 |
| | After 15 days | 1.0 | 1.1 | 1.1 |
| | After 30 days | 1.0 | 1.2 | 1.3 |
| | After 60 days | 1.0 | 1.4 | 1.6 |

(*): Ratio when the pressure drop at the start is taken as 1.0.

It is seen from the above table that when the temperature of the outlet gas is 310° C. or 320° C. beyond 300° C., the pressure drops 60 days later are larger than that when the temperature of the outlet gas is 290° C. Usually, when this ratio reaches 2.0, the operation has to be stopped. It is evident therefore that such a situation will arise earlier in Comparative Examples 5 and 6 than in Example 3.

What is claimed is:

1. A method of isolating and recovering methacrylic acid from a methacrylic acid-containing reaction product gas resulting from the vapor-phase catalytic oxidation of isobutylene, tertiary butanol or isobutyraldehyde, which comprises introducing the reaction product gas comprising methacrylic acid and various by-products including high boiling substances at a high temperature of 250° to 300° C. into a cooling zone constructed of sieve trays without a downcomer, rapidly cooling the gas therein to a temperature of not more than 100° C. to condense methacrylic acid and thus isolate methacrylic acid, while also converting the high boiling substances to fumes, thereafter introducing the cooled gas containing said fumes into a venturi scrubber, contacting it therein with an aqueous medium to remove said fumes, finally introducing the treated gas into a methacrylic acid-absorbing zone constructed of sieve trays without a downcomer and absorbing methacrylic acid by absorption into an aqueous medium.

2. The method of claim 1 wherein a cooled aqueous solution of methacrylic acid is fed as a cooling medium into the cooling zone to contact the reaction product gas directly with it and thereby cool it rapidly.

3. The method of claim 1 wherein the aqueous medium for absorption of methacrylic acid is water or an aqueous solution of methacrylic acid.

4. The method of claim 1 wherein the aqueous medium with which the cooled gas is contacted in the venturi scrubber for removing solids is an aqueous solution of methacrylic acid.

5. The method of claim 2 wherein the reaction product gas is introduced into the cooling zone near the bottom thereof and the cooling medium is introduced into the cooling zone near the top thereof whereby the cooling medium and the reaction product gas contact each other is countercurrent flow.

* * * * *